United States Patent [19]

Horii

[11] Patent Number: 5,004,998

[45] Date of Patent: Apr. 2, 1991

[54] ION-MEASURING APPARATUS FOR USE IN PROCESS

[75] Inventor: Yoshio Horii, Miyanohigashi, Japan

[73] Assignee: Horiba, Ltd., Kyoto, Japan

[21] Appl. No.: 447,221

[22] Filed: Dec. 7, 1989

[30] Foreign Application Priority Data

Dec. 14, 1988 [JP] Japan ................. 63-316778

[51] Int. Cl.$^5$ ............... G08B 21/00; G01N 27/26
[52] U.S. Cl. ................... 340/507; 204/401; 324/537; 364/497; 364/551.01
[58] Field of Search .............. 204/401, 416, 433, 412, 204/406; 364/497, 551.01; 324/438, 512, 537; 73/1 R; 340/506, 537, 507

[56] References Cited

U.S. PATENT DOCUMENTS

| | | | |
|---|---|---|---|
| 4,337,516 | 6/1982 | Murphy et al. | 364/551.01 |
| 4,402,054 | 8/1983 | Osborne et al. | 364/551.01 X |
| 4,686,011 | 8/1987 | Jäckle | 204/401 X |
| 4,734,184 | 3/1988 | Burleigh et al. | 204/409 |
| 4,777,444 | 10/1988 | Beijk et al. | 324/439 |

FOREIGN PATENT DOCUMENTS 637538 1/1964 Belgium .
3220327 12/1982 Fed. Rep. of Germany .

Primary Examiner—G. L. Kaplan
Attorney, Agent, or Firm—Price, Gess & Ubell

[57] ABSTRACT

An ion-measuring apparatus for use in processes, characterized by comprising 3 or more ion-measuring electrodes for measuring a same one ion contained in a same one sample, means for computing a mean value of measured values obtained by means of said ion-measuring electrodes, an indicating portion for indicating the computed result, means for judging an existence of an abnormality in the ion-measuring electrodes and an alarm for emitting a maintenance alarm when the abnormality occurs in any one of the ion-measuring electrodes so that the ion-measuring electrode, which has been judged to be abnormal, may be excluded to continue a measurement by means of remaining ion-measuring electrodes.

24 Claims, 10 Drawing Sheets

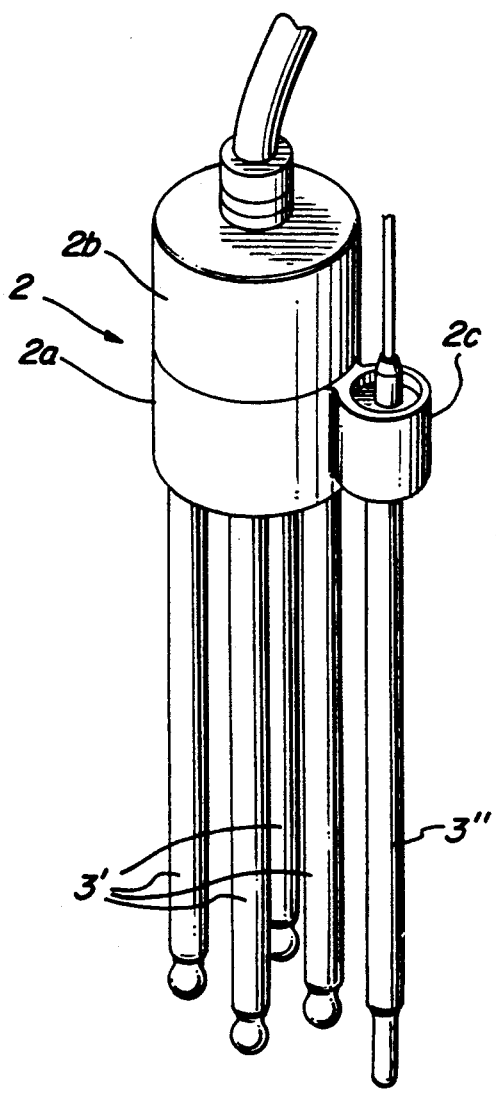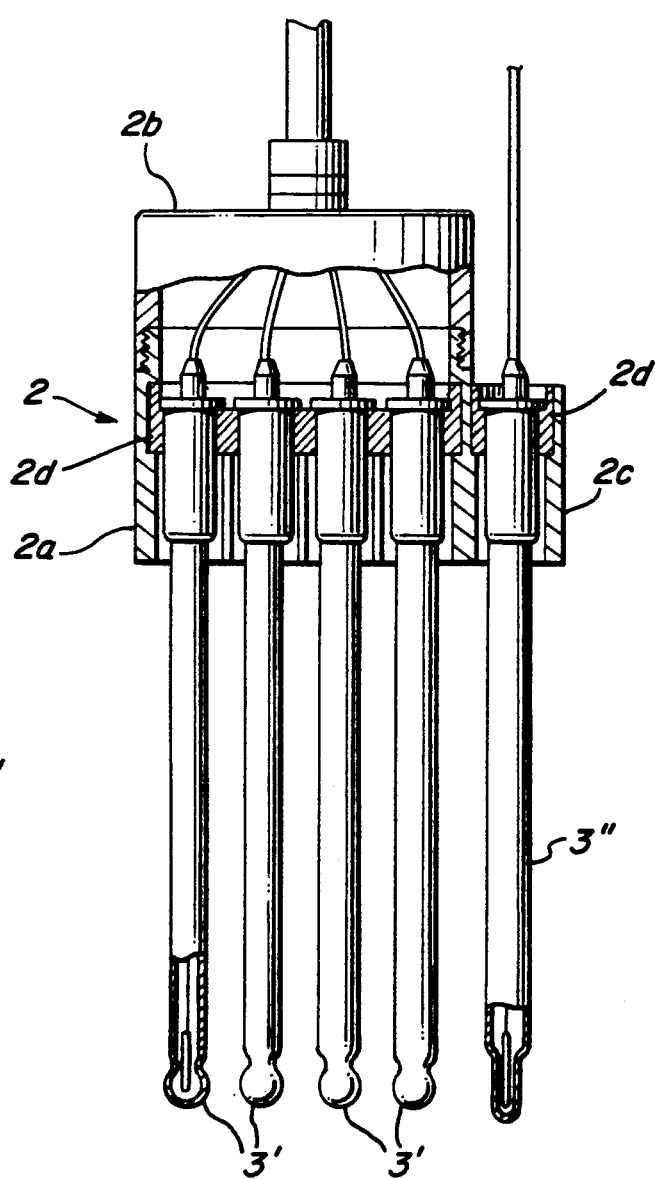

ION-MEASURING APPARATUS FOR USE IN PROCESS

BACKGROUND OF THE INVENTION

1. Field of the Invention

The present invention relates to an ion-measuring apparatus adapted to measure concentrations of $H^+$, $Na^+$, $K^+$ or other ions contained in a sample and capable of conducting a process control on the basis of the results of the measurement.

2. Description of the Prior Art

In the conventional ion-measuring apparatus for use in processes, usually not only a calibration of an ion-measuring electrode is periodically conducted but also a manual analysis is conducted by means of a separate measuring apparatus in a periodical maintenance to confirm a reliability of a measured value obtained by the ion-measuring electrode on the basis of a correlation between the measured value and the resulting analytical value.

In the above described conventional example, it is necessary to previously determine a maintenance period and periodically conduct the maintenance of the ion-measuring electrode but this maintenance period has been set considerably early than a useful life time of the ion-measuring electrode in anticipation of considerable safety.

Accordingly, it has been necessary that a worker required for maintenance must go to a measuring spot in a short period, in short before an actual occurrence of abnormality in the ion-measuring electrode, and, in the case where an actual abnormality has occurred in the ion-measuring electrode by the damage, contamination and the like of the ion-measuring electrode, a worker must instantly deal with the abnormality whether it is a holiday or midnight.

SUMMARY OF THE INVENTION

The present invention has been achieved in view of the above described conventional disadvantages and it is an object of the present invention to provide an ion-measuring apparatus for use in processes capable of increasing the maintenance period of the ion-measuring electrode and dealing with the abnormality with time to spare even though the abnormality occurs in the electrode.

It is another object of the present invention to provide an inexpensive ion-measuring apparatus having the above described advantages.

In order to achieve the above described objects, the present invention takes the following technical measures. That is to say, an ion-measuring apparatus for use in processes according to the present invention comprises 3 or more ion-measuring electrodes for measuring the same one ion contained in the same one sample, means for calculating a mean value of measured values by these ion-measuring electrodes, means for indicating a result of the calculation, means for judging an existence of the abnormality in these ion-measuring electrodes and an alarm portion for emitting a maintenance alarm when the abnormality occurs in any one of the ion-measuring electrodes and is characterized in that the ion-measuring electrode, which has been judged to be abnormal, is excluded and the measurement is continued by means of remaining ion-measuring electrodes.

The ion-measuring apparatus according to the present invention may be provided with a spare ion-measuring electrode in addition to the above described construction so that the ion-measuring electrode, which has been judged to be abnormal, may be switched to the spare ion-measuring electrode to continue the measurement by means of said spare ion-measuring electrode and the remaining ion-measuring electrodes.

In addition, the ion-measuring apparatus according to the present may comprise 2 sets of 3 or more ion-measuring electrodes for measuring the same one ion contained in the same one sample, means for alternately changing over 2 sets of ion-measuring electrodes to a measuring condition, in which the ion-measuring electrodes are brought into contact with the sample, and an awaiting condition, in which the ion-measuring electrodes are not brought into contact with the sample, means for calculating a mean value of measured values obtained by the ion-measuring electrodes existing under the measuring condition, a portion for indicating the result of calculation, means for judging an existence of an abnormality in the ion-measuring electrodes existing under the awaiting condition and an alarm portion for emitting a maintenance alarm when the abnormality occurs in any one of the ion-measuring electrodes so that the ion-measuring electrode, which has been judged to be abnormal, may be excluded to continue the measurement by means of the remaining ion-measuring electrodes.

Said ion-measuring electrodes may be rod-like composite electrodes and sheet-like composite electrodes integrally comprising an ion-selective electrode and a reference electrode.

In addition, said 3 or more ion-measuring electrodes may comprise 3 or more ion-selective electrodes and one reference electrode to commonly use one reference electrode for the respective ion-measuring electrodes. Said 2 sets of ion-measuring electrodes may comprise 2 sets of 3 or more ion-selective electrodes and one reference electrode to commonly use one reference electrode for the respective ion-selective electrodes.

With the ion-measuring apparatus for use in processes having the above described construction, if no abnormality occurs in all ion-measuring electrodes, a mean value of the measured values obtained by the respective electrodes is indicated and the process control is conducted on the basis of the indicated mean value.

If the abnormality occurs in any one of the electrodes, the maintenance alarm is emitted but the electrode, which has been judged to be abnormal, is excluded to continue the measurement by means of the remaining normal electrodes or the remaining normal electrodes and the spare electrode.

Accordingly, even though the maintenance alarm is emitted, in short the actual abnormality occurs in the electrode, the process control is not hindered, so that the maintenance of the electrodes can be conducted with a time to spare.

In addition, the maintenance alarm is emitted at a point of time when the actual abnormality occurs in the electrode, so that it is unnecessary to determine the maintenance period so that the maintenance may be conducted before the occurrence of the abnormality in the electrode, whereby the maintenance period can be increased.

BRIEF DESCRIPTION OF THE DRAWINGS

One preferred embodiment of the present invention is shown in FIGS. 1, 2, in which

Another preferred embodiment of the present invention is shown in FIGS. 3, 4, in which FIG. 3 is a perspective view showing principal parts; and FIG. 4 is a partially cut-off front view showing the principal parts.

Another preferred embodiment of the present invention is shown in FIGS. 11 to 14, in which

DESCRIPTION OF THE PREFERRED EMBODIMENTS

The preferred embodiments of the present invention will be below described with reference to the drawings.

Figure 1:
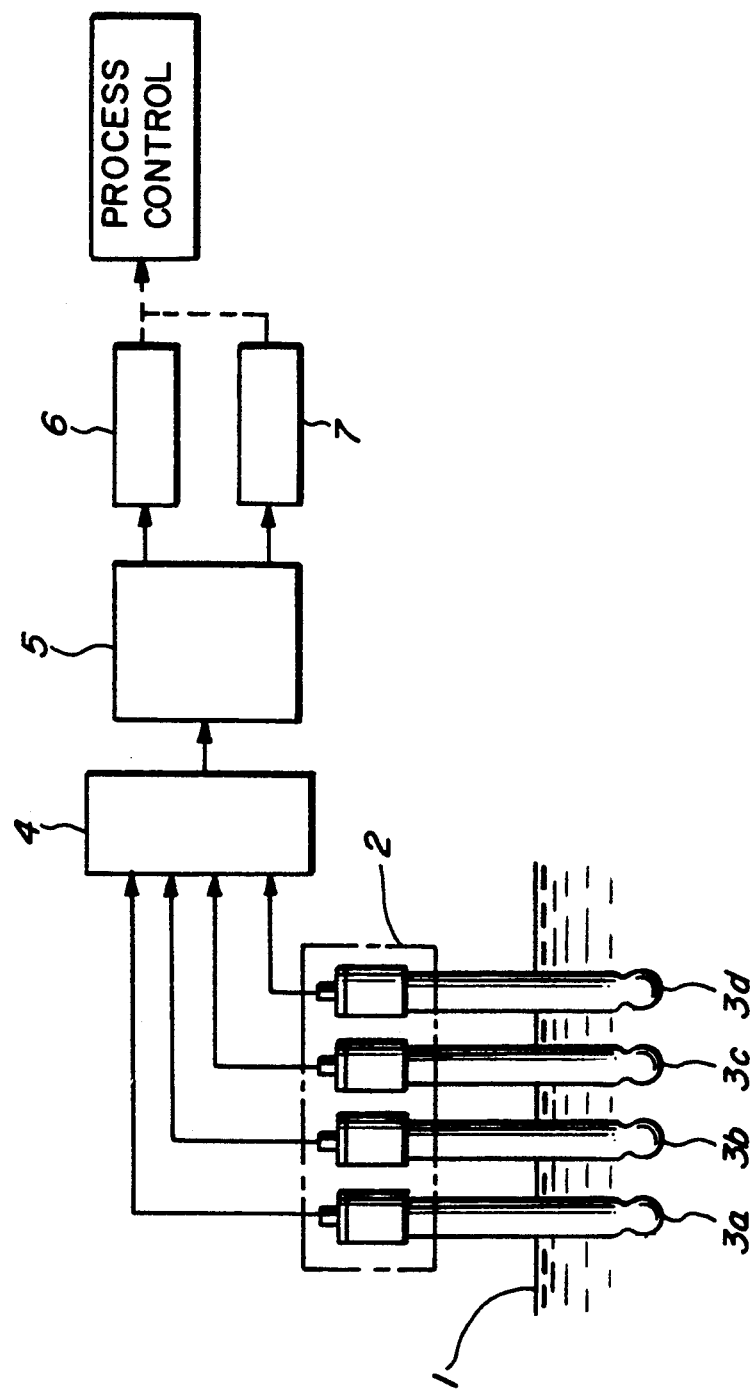
FIG. 1 is a rough block diagram showing a pH measuring apparatus for use in processes.
Figure 2:
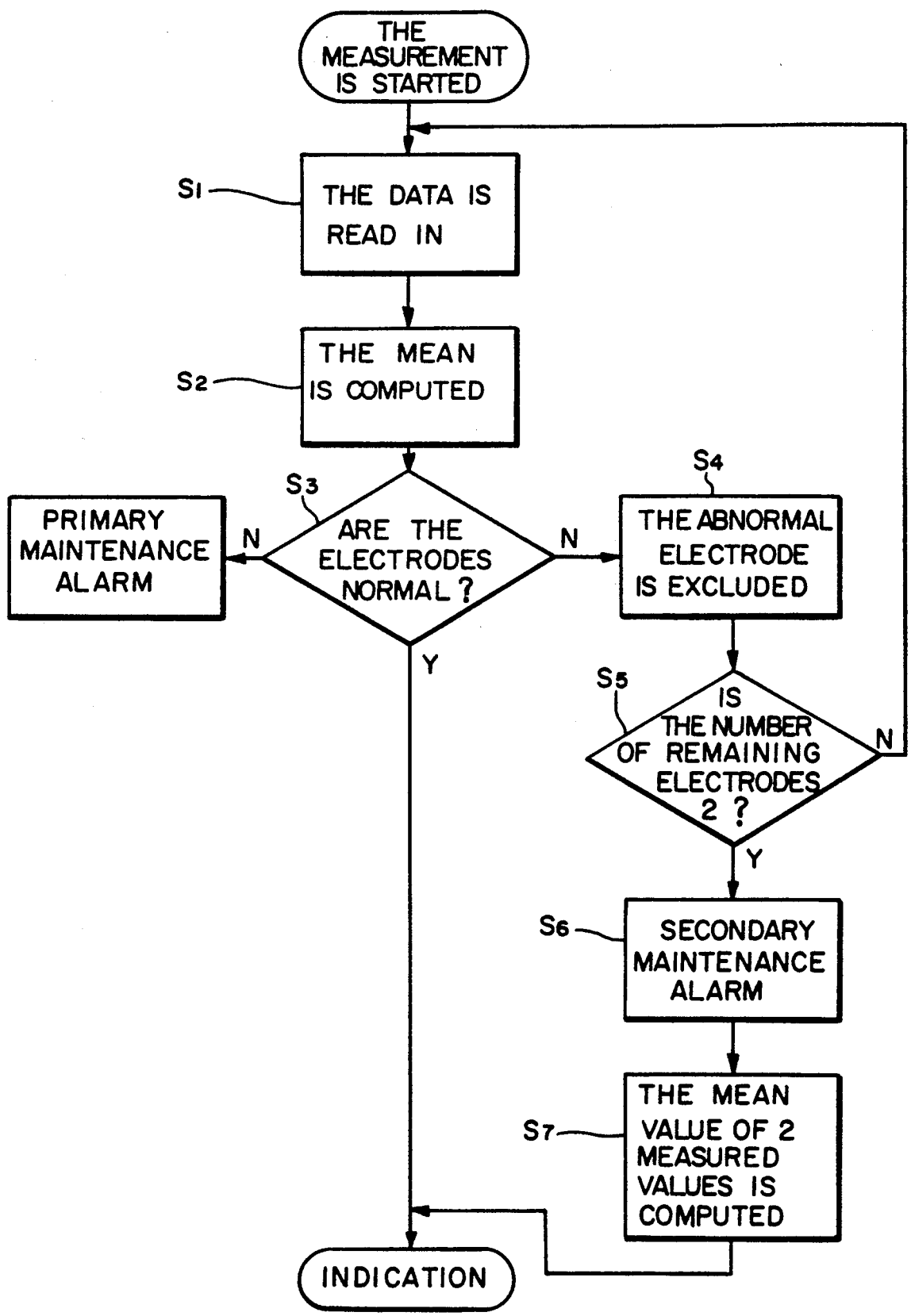
FIG. 2 is a flow chart for describing an operation of the pH-measuring apparatus for use in processes.

FIG. 1 shows a pH-measuring apparatus for use in processes and FIG. 2 is a flow chart for describing an operation of said apparatus. Referring now to FIGS. 1, 2, reference numeral 1 designates a sample, reference numeral 2 designating an immersion electrode-holder, and reference numerals 3a, 3b, 3c, 3d designating 3 or more (4 in this preferred embodiment) pH-measuring electrode. Said electrodes 3a, 3b, 3c, 3d are held by one electrode-holder 2 so as to be separately mounted and detached. All of them are used for the measurement of pH of the same one sample 1. Reference numeral 4 designates changeover means for selectively taking measured signals by the respective electrodes 3a, 3b, 3c, 3d in a computing portion 5. Mean value-calculating means is composed of said change-over means 4 and said computing portion 5. That is to say, the measured signals by the respective electrodes 3a, 3b, 3c, 3d are put in the computing portion 5 through the changeover means 4 in turn where the mean value of the pH-measured values by the respective electrodes 3a, 3b, measured values by the respective electrodes 3a, 3b, 3c, 3d is computed. And, a signal corresponding to said mean value is put out from an indicating portion 6 and an appointed process control (for example an automatic regulation of pH in a plating bath and the like) is conducted on the basis of said output signal. Said computing portion 5 is provided with means for judging the existence of the abnormality in the electrodes 3a, 3b, 3c, 3d on the basis of the measured signals by the respective electrodes a, 3b, 3c, 3d. If the abnormality occurs in any one of the electrodes 3a, 3b, 3c, 3d, the electrode, which has been judged to be abnormal, is excluded (the measured signal is cut) and the measurement of pH of said sample 1 is continued by the remaining electrodes. Reference numeral 7 designates an alarm portion composed of a lamp and the like. When the abnormality occurs in any one of the electrodes 3a, 3b, 3c, 3d, a primary maintenance alarm (that is a previous warning alarm informing the approach of the maintenance time, for example this is realized by lighting a yellow lamp) is emitted and when the abnormality occurs in two electrodes, in other words merely two electrodes are normal, a secondary maintenance alarm (for example the lighting of a red lamp) is emitted.

Next, an operation of the above described apparatus is described with reference to FIG. 2.

When the apparatus is installed at first, a zero point and a sensitivity are calibrated by the use of two kinds of standard solution (the first standard solution having a pH of 7 and the second standard solution having a pH close to a pH of the sample 1) prior to the measurement. The characteristics of the respective electrodes 3a, 3b, 3c, 3d obtained in this calibration, in short an unsymmetrical electric potential (an electromotive force at a pH of 7), a sensitivity and a response time (a time from a point of time when the first standard solution is changed over to the second standard solution until a point of time when the output is stabilized) are memorized in a memory of said computing portion 5 and used as data for judging the useful life time of the respective electrodes in the maintenance which will be conducted later.

After finishing the calibration, all of the electrodes 3a, 3b, 3c, 3d are immersed in the sample 1 to start the measurement.

The measured signals (voltages on a mV unit) by four electrodes 3a, 3b, 3c, 3d are read in the computing portion 5 in turn through the change-over means 4 (Step $S_1$).

In the computing portion 5, the mean value (pHm) of the measured values by four electrodes 3a, 3b, 3c, 3d is computed (Step $S_2$).

Subsequently, the existence of the abnormality in the electrodes 3a, 3b, 3c, 3d is judged (Step $S_3$).

This judgment is conducted as follows:

That is to say, a potential difference $\Delta$ pHx of the respective electrodes 3a, 3b, 3c, 3d relative to the mean value (pHm) computed in the Step $S_2$ (this is a general name of the potential difference $\Delta$ pHa of the electrode 3a, the potential difference of $\Delta$ pHb of electrode 3b, the potential difference $\Delta$ pHc of the electrode 3c and the potential difference $\Delta$ pHd of the electrode 3d.) = pHm - pHx is computed and if said potential difference $\Delta$ pHx is within an allowable range, the electrode is judged to be normal while if said potential difference exceeds the allowable range, the electrode is judged to be abnormal. For example, Provided that the measured value by a certain electrode 3a is pHa when the mean value is pHm, pHm - pHa = $\Delta$ pHa is determined and if this is within a previously set allowable range (for example $\pm 0.1$ pH corresponding to about $\pm 6$ mV), said electrode 3a is judged to be normal while if this exceeds the allowable range ($\pm 0.1$ pH corresponding to about $\pm 6$ mV), said electrode 3a is judged to be abnormal.

In the case where all of the electrodes 3a, 3b, 3c, 3d are judged to be normal, the mean value (pHm) obtained by Step $s_2$ is converted into a pH unit and put in the indicating portion 6. The process control is conducted on the basis of the signal put out from the indicating portion 6.

When any one of the electrodes $3a$, $3b$, $3c$, $3d$ is judged to be abnormal, the primary maintenance alarm is emitted from the alarm portion 7 and simultaneously the electrode, which has been judged to be abnormal, is excluded (the measured signal is cut) (Step $S_4$)

Then, it is judged whether two electrodes are active or not (Step $S_5$). In the case where 3 or more electrodes are active, the procedure is returned to Step $S_1$, so that the measurement by means of 3 or more electrodes is continued through Steps $S_2$, $S_3$ and $S_4$ and the process control is continued on the basis of the signal of the mean value (pHm) put out from the indicating portion 6.

In the case where 2 electrodes still active, the secondary maintenance alarm is emitted from the alarm portion 7 (Step $S_6$) and the mean value of the measured values by said 2 electrodes is computed (Step $S_7$). Subsequently, said mean value is converted into a pH unit and put in the indicating portion 6. The process control is continued on the basis of the signal put out from the indicating portion 6.

And, if the secondary maintenance alarm has been activated, the worker required for maintenance goes to the measuring spot to conduct the maintenance, the exchange and the like of the electrode, which has been judged to be abnormal and excluded, without interrupting the continued measurement by means of the 2 remaining electrodes. In this case, it can be determined whether said electrode should be exchanged or not by conducting the calibration by means of the first and second standard solutions to measure the characteristics of the electrode, which has been judged to be abnormal and excluded, (unsymmetric electric potential, sensitivity, response speed), and comparing these with the initial values (the above described data for judging a useful life time) to confirm to what extent these characteristics are varied from the initial values (whether they reach the previously set control values or not).

In addition, although a rod-like composite electrode integrally comprising a glass electrode, which is an ion-selective electrode, and a reference electrode is used as the electrodes $3a$, $3b$, $3c$, $3d$, respectively, the ion-selective electrode and the reference electrode may be separately used (in the event that the temperature of the sample is not constant, also a temperature compensating electrode is integrated according to circumstances). When the ion-selective electrode and the reference electrode are separately used, said electrodes $3a$, $3b$, $3c$, $3d$ may be composed of 3 or more (4 in the preferred embodiment shown in the drawing) glass electrodes 3' and one reference electrode 3" and one reference electrode 3" may be commonly used for the respective glass electrodes 3', as shown in FIGS. 3 and 4. With such the construction, not only the expense for the electrodes can be saved but also the standard electric potential can be fixed due to the common use of the reference electrode 3" and thus the accuracy of measurement can be improved. Referring to FIGS. 3 and 4, reference numeral $2a$ designates a holder body, reference numeral $2b$ designating a screw type cap, reference numeral $2c$ designating a reference electrode holder provided in said holder body $2a$, and reference numeral $2d$ designating a packing made of rubber and the like. One electrode holder 2 is composed of said members $2a$, $2b$, $2c$ and $2d$.

Figure 5:
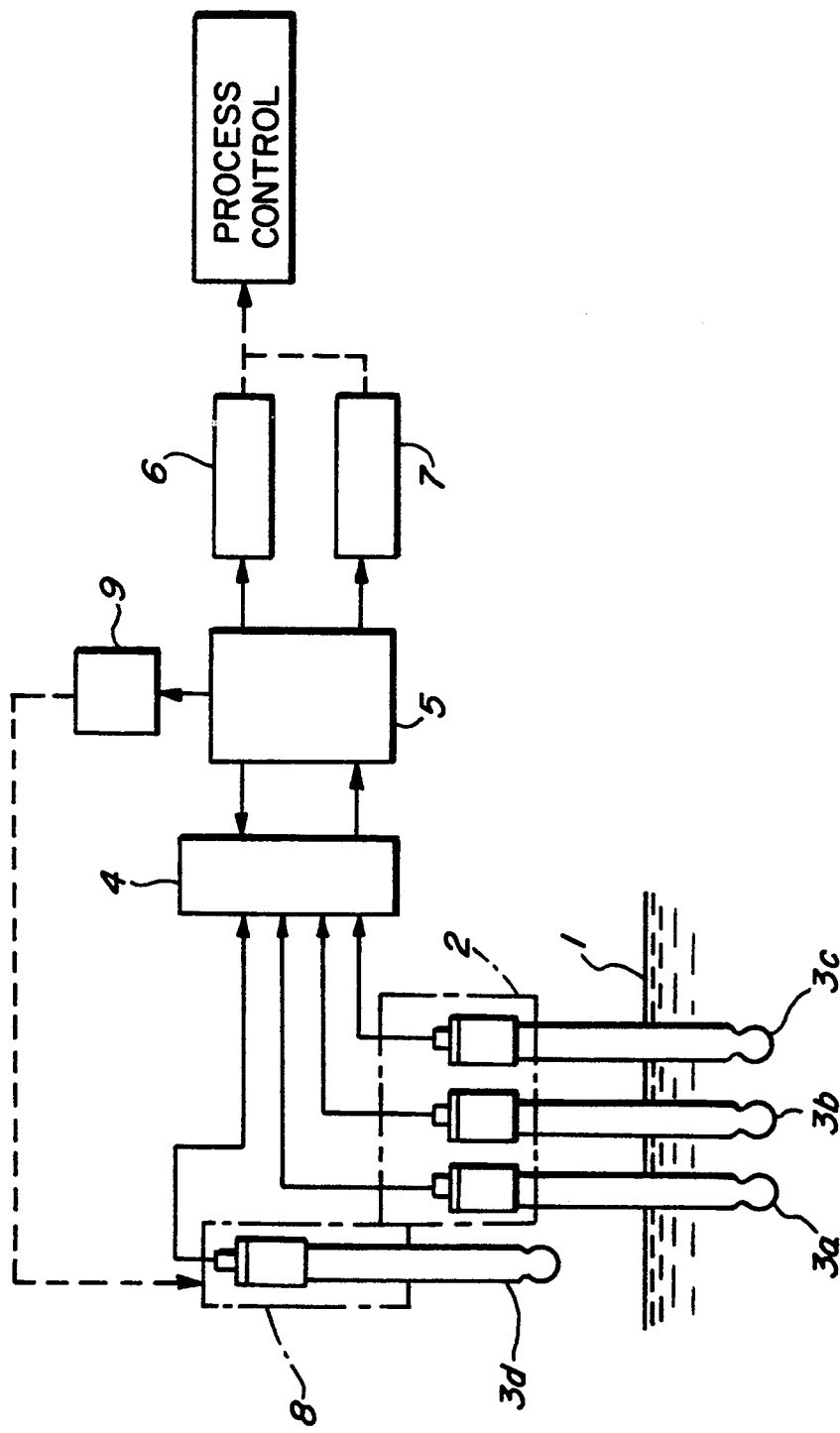
FIG. 5 is a rough block diagram showing a pH measuring apparatus for use in processes according to another preferred embodiment of the present invention.

FIG. 5 is a rough block diagram showing a pH-measuring apparatus for use in processes according to another preferred embodiment of the present invention. In this pH-measuring apparatus for use in processes, 3 or more (3 in the preferred embodiment shown in the drawing) pH-measuring electrodes $3a3b$, c having the same one construction and type of spare electrode $3d$ are mounted on an electrode holder 2, an elevating device 8 for moving said spare electrode d from a position above a sample 1 to a position where the spare electrode $3d$ is immersed in the sample 1 being provided, and the process control being conducted on the basis of a mean value of measured values by said electrodes $3a$, $3b$, $3c$. When an abnormality occurs in any one of these electrodes $3a$, $3b$, $3c$, an alarm 6 emits a primary maintenance alarm and simultaneously an electrode, which has been judged to be abnormal, is automatically changed over to the spare electrode $3d$ to continue the measurement by means of said spare electrode $3d$ and the 2 remaining electrodes. In addition, when an abnormality occurs in any one of the 3 electrodes (the spare electrode and 2 remaining electrodes) used for the measurement under the above described condition, the alarm 6 emits a secondary maintenance alarm. Reference numeral 4 designates a change-over device for selectively taking measured signals by the electrodes $3a$, $3b$, $3c$, $3d$ in a computing portion 4 and reference numeral 9 designates a controller for said elevating device 8. Other constituent members are same as in the preceding preferred embodiment.

Figure 6:
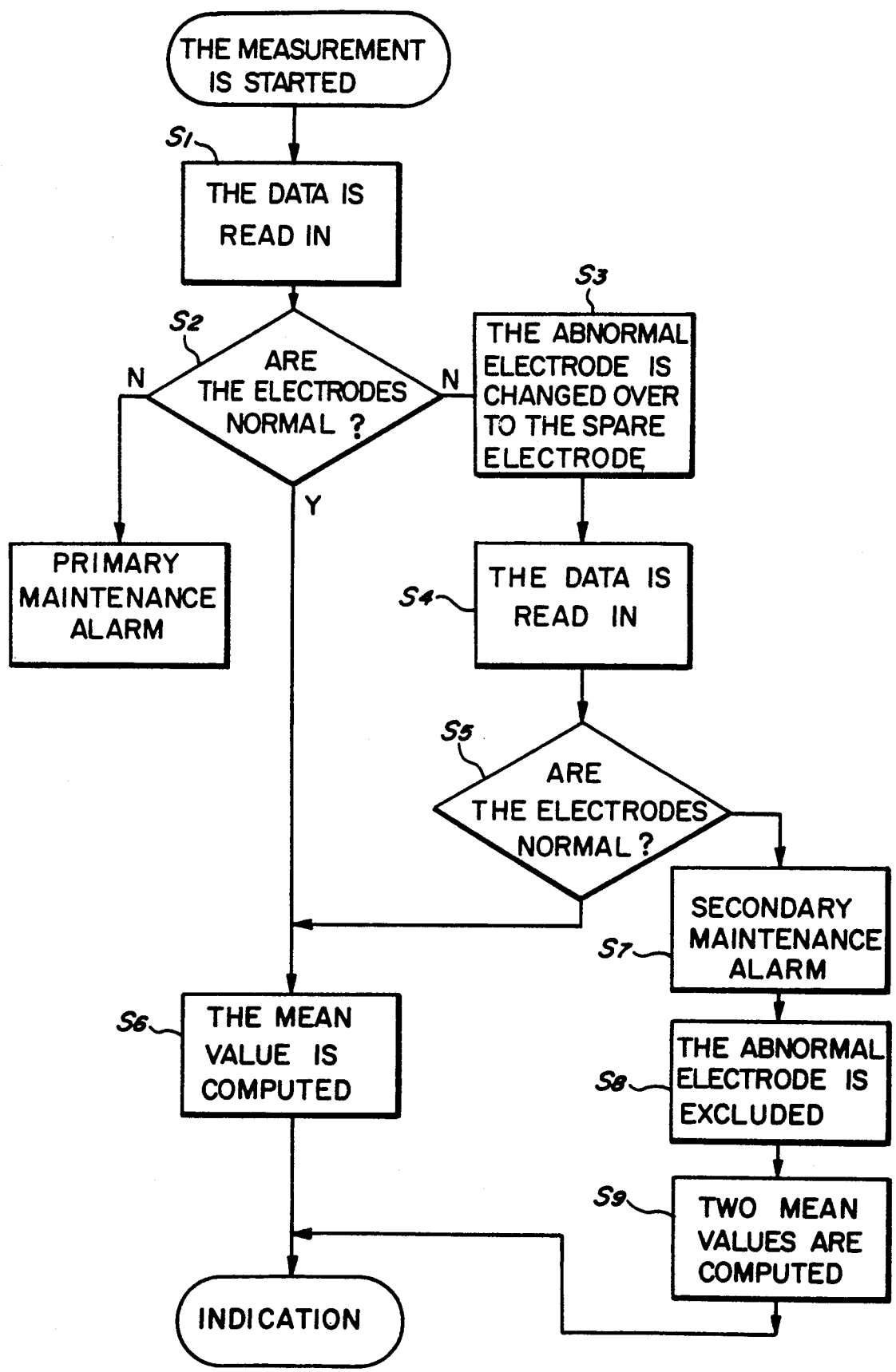
FIG. 6 is a flow chart for describing an operation of the apparatus shown in FIG. 5.

An operation of the above described apparatus is described with reference to FIG. 6 as follows:

All of the electrodes $3a$, $3b$, $3c$, $3d$ are calibrated and the data for judging the useful life time are obtained. Subsequently, the measurement is started by means of 3 electrodes $3a$, $3b$, $3c$.

Measured signals by 3 electrodes $3a$, $3b$, $3c$ are read in a computing portion 5 in turn through the change-over device 4 (Step $S_1$).

In the computing portion 5, a comparison of the measured signals by the respective electrodes $3a$, $3b$, and $3c$ is conducted to judge the existence of any abnormality (Step $S_2$). That is to say, if the measured signals by the 3 electrodes $3a$, $3b$, $3c$ are similar to each other, all of the electrodes are judged to be normal while if merely the measured signal by any one of the electrodes is greatly different from the measured signals by 2 other electrodes, said one electrode is judged to be abnormal and the 2 remaining electrodes are judged to be normal In the case where all of the electrodes $3a$, $3b$, $3c$ are judged to be normal, a mean value of the measured values by these electrodes $3a$, $3b$, $3c$ is computed (Step $S_6$) and the computed mean value is converted into a pH unit to be put in an indicating portion 6. The process control is conducted on the basis of the signal put out from the indicating portion 6.

If any one electrode is judged to be abnormal, an alarm 7 emits a primary maintenance alarm and simultaneously the electrode, which has been judged to be abnormal, is changed over to the spare electrode $3d$ (Step $S_3$). That is to say, the measured signal from the electrode, which has been judged to be abnormal, is suspended and simultaneoulsy the elevating device 8 is operated to descend the spare electrode $3d$ to a position where the spare electrode is immersed in the sample 1.

Subsequently, the measured signals by the 2 remaining electrodes and the spare electrode 3d are read in the computing portion 5 in turn through the change-over device 4 (Step S$_4$).

In the computing portion 5, a comparison of these 3 electrodes (2 remaining electrodes and the L spare electrode 3d) is conducted to judge the existence of abnormality (Step S$_5$).

In the case where all of the electrodes are judged to be normal, the procedure is made to progress to Step S$_6$. But, if any one electrode is judged to be abnormal, the alarm 7 emits a secondary maintenance alarm (Step S$_7$) to electrode, which has been judged to be abnormal, (to cut the measured signal) (Step S$_8$) and compute a mean value of the measured values by the 2 remaining electrodes (Step S$_9$). The process control is continued on the basis of this mean value.

And, when the secondary maintenance alarm is emitted, the worker required for maintenance goes to the measuring spot to conduct the maintenance, exchange and the like of the electrode, which has been judged to be abnormal and excluded, within the continued measurement by means of the 2 remaining electrodes.

According to the present preferred embodiment, the spare electrode 3d is held under the condition that it is not brought into contact with the sample 1 during the normal measurement by means of the electrodes 3a, 3b, 3c while it is immersed in the sample 1 when it is actually required, so that an advantage occurs in that the deterioration of the spare electrode 3d due to hindrances, soils and the like in the sample 1 can be prevented.

Figure 7:
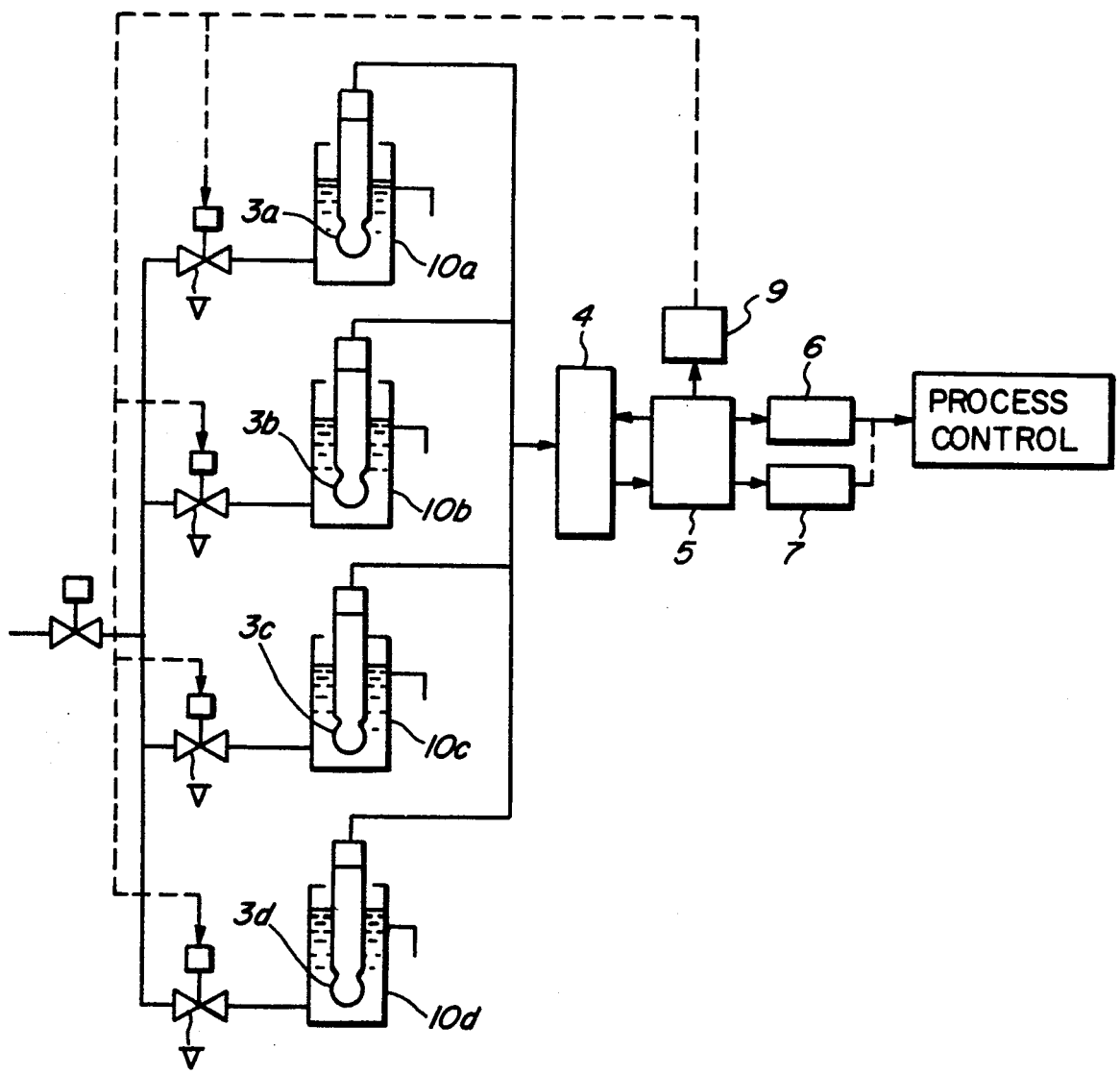
FIG. 7 is a rough block diagram showing a pH-measuring apparatus for use in processes according to another preferred embodiment of the present invention.

In addition, in the case where 4 or more electrodes other than the spare electrode 3d are used, a control program, in which the electrodes which have been judged to be abnormal are excluded one by one until 3 electrodes are remained, is added. Although a rod-like composite electrode integrally comprising a glass electrode and a reference electrode is used as the electrodes 3a, 3b, 3c, 3d, respectively, in the preferred embodiment shown in the drawing, the glass electrode and the reference electrode may be separated. In addition, similarly to the preferred embodiment described with reference to FIGS. 3 and 4, one reference electrode may be commonly used for the respective glass electrodes. Furthermore, also a flow through type apparatus as shown in FIG. 7 can be used. That is to say, respective electrodes 3a, 3b, 3c, 3d are separately installed in respective electrode chambers 10a, 10b, 10c, 10d and electro-magnetic valves V are provided in sample-sampling passages communicating with the respective electrode chambers 10a, 10b, 10c, 10d. When any one electrode is judged to be abnormal, the electro-magnetic valve V of the electrode chamber corresponding to the electrode, which has been judged to be abnormal, is closed by a signal from a controller 9 and simultaneously the electro-magnetic valve V of the electrode chamber 10d for use in the spare electrode 3d is opened.

Figure 8:
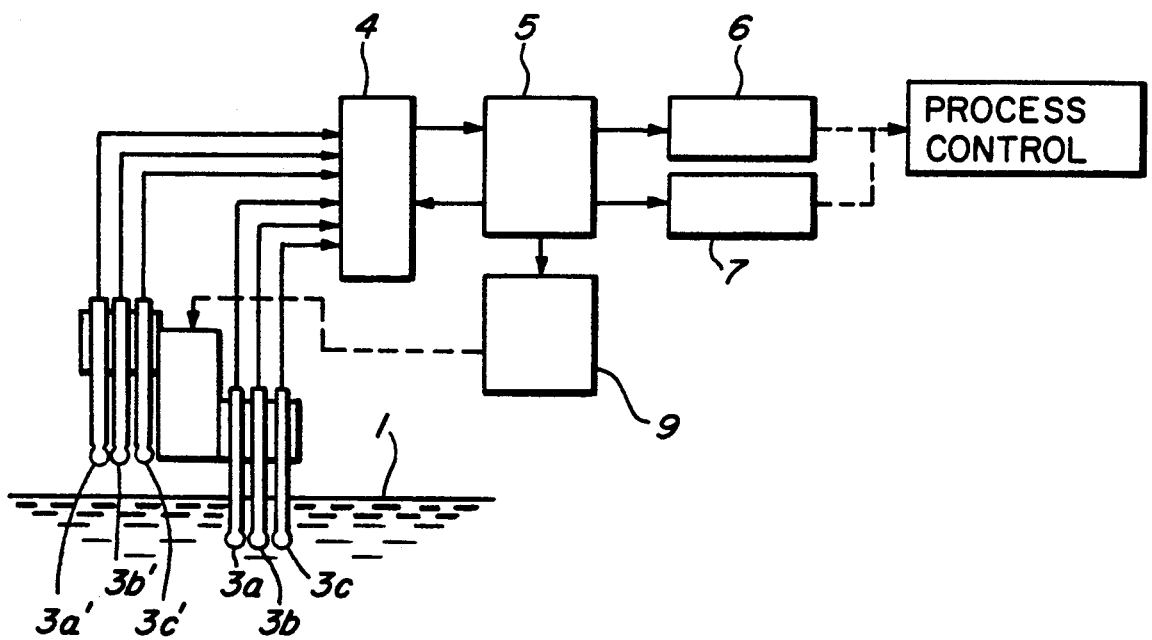
FIG. 8 is a rough block diagram showing a pH-measuring apparatus for use in processes according to another preferred embodiment of the present invention.
Figure 9:
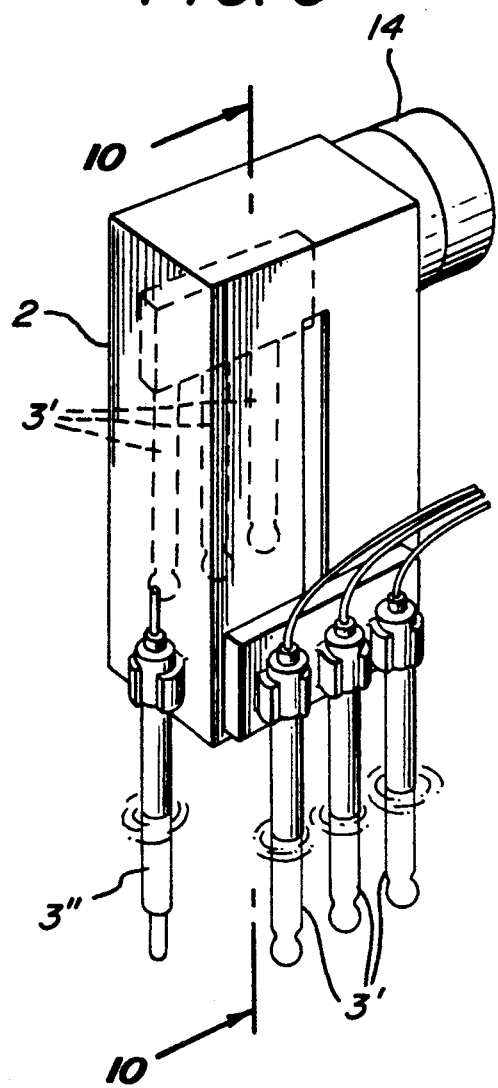
FIG. 9 is a perspective view showing principal parts of the apparatus shown in FIG. 8.

FIGS. 8 and 9 show a further preferred embodiment of the present invention.

Figure 10:
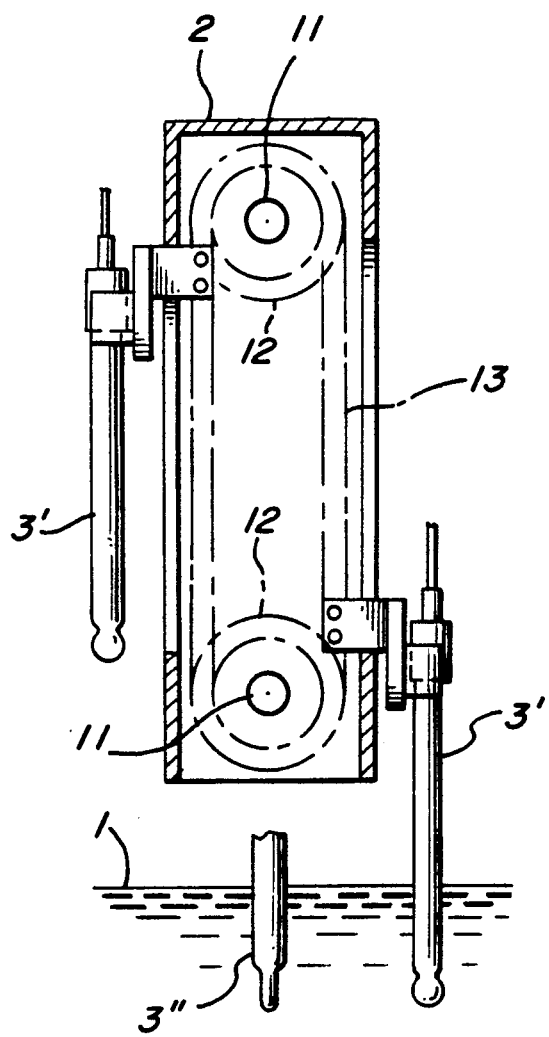
FIG. 10 is a longitudinally sectioned side view showing the principal parts of the apparatus shown in FIG. 8.
Figure 11:
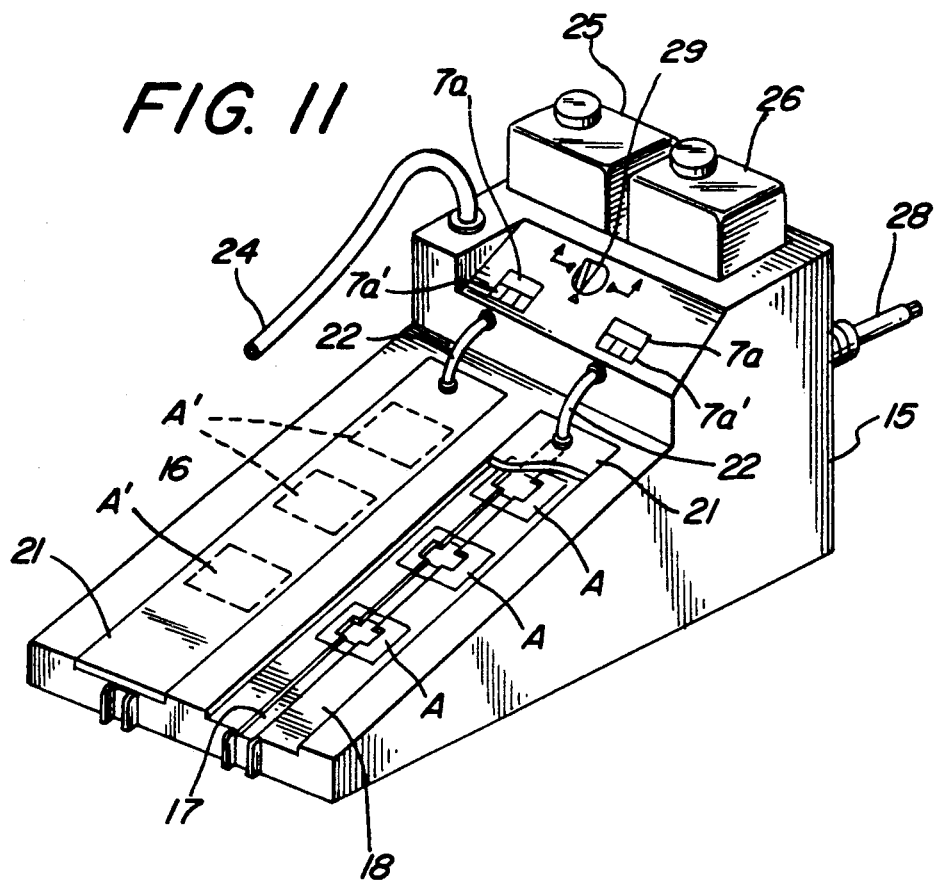
FIG. 11 is a perspective view showing a pH-measuring apparatus for use in processes.

An apparatus according to this preferred embodiment comprises 2 sets of 3 or more pH-measuring electrodes 3a, 3b, 3c, 3a', 3b', 3c' having the same type of construction, means for alternately changing over said 2 sets of electrodes (3a, 3b, 3c and 3a', 3b', 3c') to a measuring condition, in which they are brought into contact with a sample 1, and a waiting condition, in which they are not brought into contact with the sample 1, in an appointed period, means for computing a mean value of measured values by the electrodes (3a, 3b, 3c or 3a', 3b', 3c') existing under the measuring condition, an indicating portion 6 for indicating a computed result, means for judging an existence of abnormality in the electrodes (3a, 3b, 3c or 3a', 3b', 3c') and an alarm 7 for emitting a maintenance alarm when the abnormality occurs in any one of the electrodes and is characterized in that the electrode, which has been judged to be abnormal, is excluded to continue the measurement by means of the remaining electrodes. Although various kinds of mechanism can be adopted as the above described 2 condition change over means, in the present preferred embodiment, as shown in FIGS. 9 and 10, an endless belt 13 is extended across wheel members 12, 12 pivotally installed through horizontal shafts 11 above and below an electrode-holder 2 and 2 sets of a group of electrodes are mounted on said endless belt 13 at symmetrical positions of the endless belt 13, and a motor 14, which can be reversibly changed over, being driven on the basis of a signal from a controller 9, whereby the above described 2 condition-change over can be conducted. Other constructions are the same as in the preceding preferred embodiment.

An operation of the above described pH-measuring apparatus for use in processes is substantially the same one as that shown in FIG. 2 excepting that 2 sets of a group of electrodes are automatically changed over to a measuring condition and an awaiting condition in an appointed period, so that its description is omitted.

According to the present preferred embodiment, 2 sets of a group of electrodes are alternately used, so that the sum total of an actual operation time of the respective electrodes occupying in an operation time of the apparatus is reduced to half, whereby the maintenance period can be increased.

In addition, said electrodes 3a, 3b, 3c, 3a', 3b', 3c' may be composite electrodes and a glass electrode and a reference electrode may be separately used. In particular, in the latter case, the above described 2 sets of group of electrodes (3a, 3b, 3c) and (3a', 3b', 3c') are composed of 2 sets of broup of glass electrodes 3' and one reference electrode 3'' to commonly use one reference electrode 3'' as a reference electrode for 2 sets of group of glass electrodes 3', whereby an expense of the electrodes can be reduced, and a standard electric potential of 2 sets of group of electrodes is fixed, so that an accuracy of measurement can be improved.

FIGS. 11 to 14 show a further preferred embodiment of the present invention. The present preferred embodiment is characterized in that 2 condition-change over means for alternately changing over 2 sets of 3 or more sheet-like composite electrodes for use in a measurement of pH A, A' and 2 sets of sheet-like composite electrodes A, A' having the same type of construction to a measuring condition, in which the electrodes are brought into contact with a sample, and an awaiting condition, in which the electrodes are not brought into contact with the sample, in an appointed period, means for computing a mean value of measured values by the sheet-like composite electrodes (A or A') existing ulcer the measuring condition, an indicating portion 6, means for judging an existence of an abnormality in the sheet-like composite electrodes (A or A') existing under the measuring condition and an alarm 7 for emitting a maintenance alarm when the abnormality occurs in any one of the sheet-like composite electrodes are provided and the sheet-like composite electrode, which has been judged to be abnormal, is excluded to continue the measurement by means of the remaining sheet-like composite electrodes.

The construction of this pH-measuring apparatus for use in processes is in more detail described as follows:

That is to say, reference numeral 15 designates an apparatus body, a pair of right inclined surface 18 and left inclined surface 18 provided with a groove 17 inclined at about 15 to 25° being formed on an upper surface 16 of said apparatus body 15, and 3 or more (3 in the preferred embodiment shown in the drawings) concave portions 19 being formed along the groove 17 in the respective inclined surfaces 18. The respective sheet-like composite electrodes A, A' are detachably inserted into said concave portions 19 so that a sample-receiving concave portion(a) on an upper surface of the respective sheet-like composite electrodes A, A' may be communicated with the groove 17. Reference numeral 20 designates an elastic packing made of rubber and the like for fixing the sheet-like composite electrodes A, A' and making a circumference watertight. Reference numerals 21, 21 designate a detachable cover installed so as to be stuck to the inclined surfaces 18, 18 and to cover the groove 17 and the sample-receiving concave portion (a). Tubes 22, 22 are based through the side of an upper end of the inclination of the covers 21, 21 so that the continuously sampled sample 1 may be alternately fallen drop by drop from the tubes 22, 22 in an appointed period to alternately flow the sample 1 through both grooves 17, 17 in an appointed period (this period is set at an interval of a time required for a calibration which will be mentioned later or more). Reference numeral 23 designates a sampling pump and $V_1$, $V_2$ designate three-way electro-magnetic valves for changing over flowing directions toward the right groove 17 and the left groove 17. These members compose said 2 condition-change over means. Reference numeral 24 designates a tube for sampling the sample 1, reference numeral 25 designating a tank of a first standard solution, reference numeral 26 designating a bank of a second standard solution, reference numeral 27 designating a pump for supplying the standard solutions, and reference numeral 28 designating a signal-taking out cable for use in a process control. Reference numerals 7a, 7a designate lamps composing the alarm 7. Reference numeral 7a', 7a' designate interchange display lamps provided corresponding to the respective electrodes and they are lighted when a degree of change (deterioration) in characteristic of the respective electrodes measured in the calibration exceeds a previously set control value. $V_3$ designates a manual three-way valve for changing over the first standard solution and the second standard solution to each other and reference numeral 29 designates an operating portion of said three-way valve $V_3$.

Figure 12:
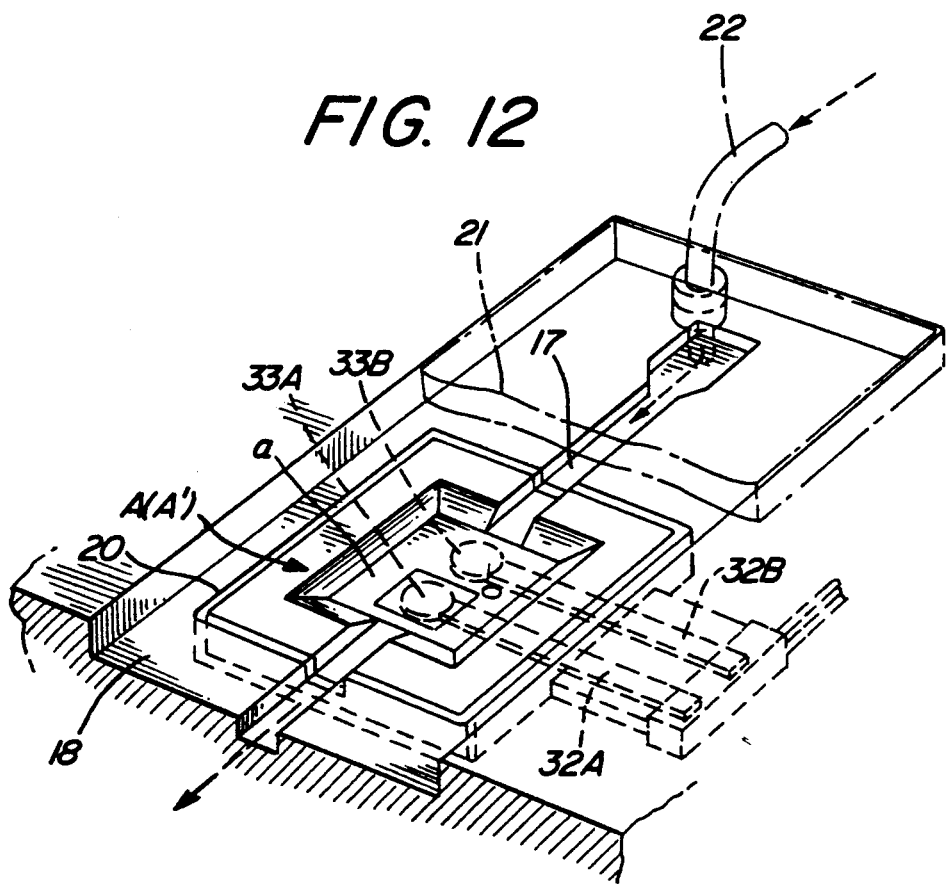
FIG. 12 is a perspective view showing principal parts.

Said sheet-like composite electrodes A, A', as an external appearance thereof is shown in FIG. 12, comprise as square portion having a reduced thickness and a terminal plate portion projected form one side of said square portion. The detailed construction is shown in FIG. 13.

Figure 13:
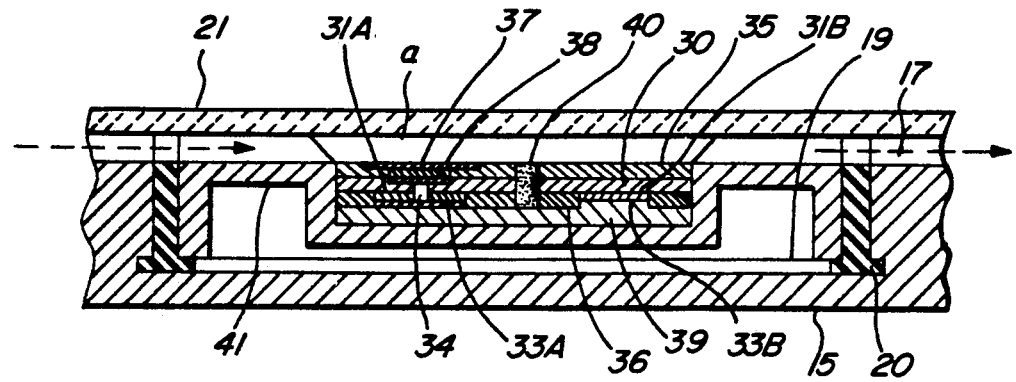
FIG. 13 is a longitudinally sectioned front view showing the principal parts.
Figure 14:
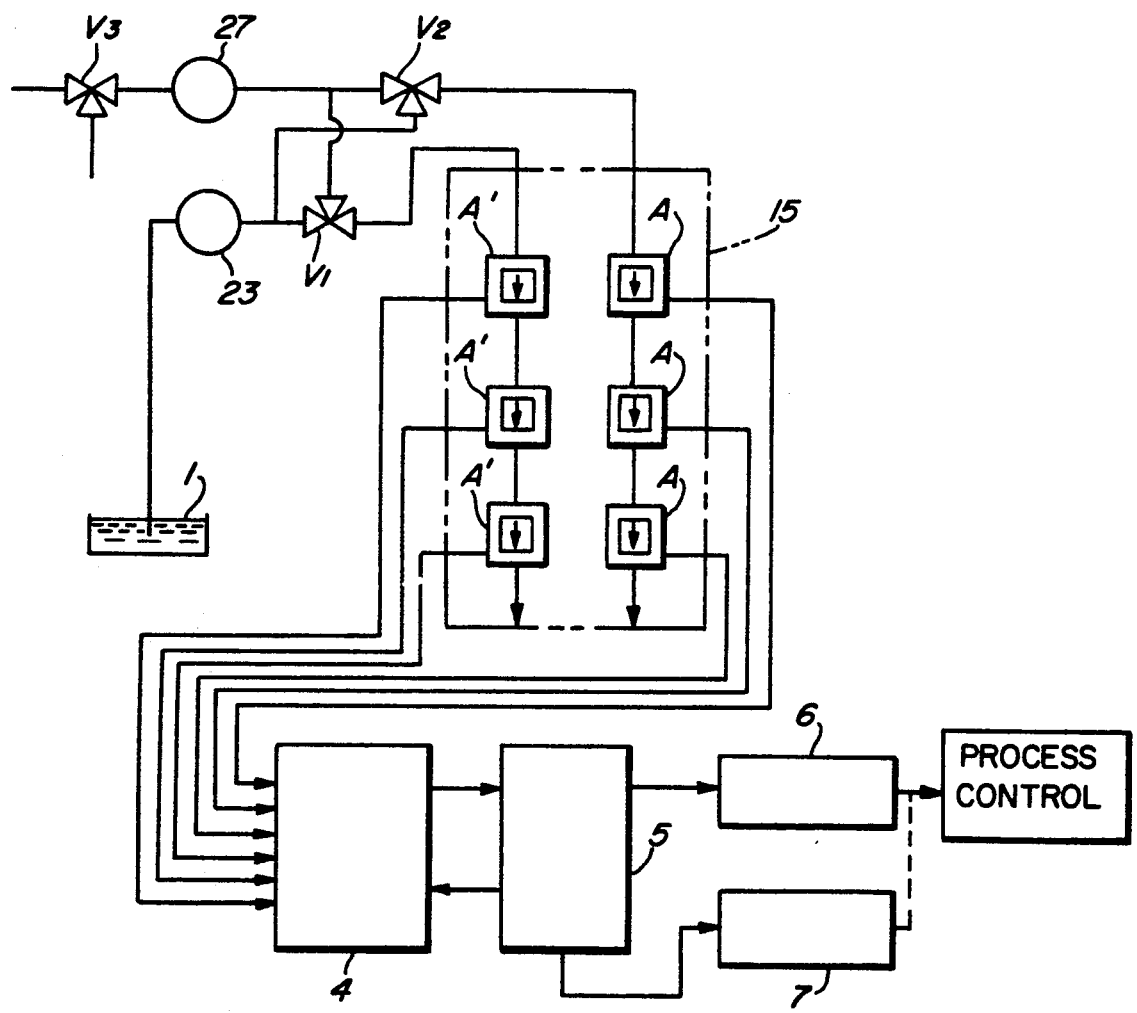
FIG. 14 is a rough block diagram showing a pH-measuring apparatus for use in processes.

Referring to FIG. 13, reference numeral 30 designates a substrate formed of material (for example polyethylene terephthalate, silica glass and the like) having a sufficiently high electrical insulating property even though they are immersed in a solution containing electrolytes. Said substrate 30 is provided with at least one pair (two pairs in case of the sheet-like composite electrodes provided with a temperature compensating electrode integrated therewith) of electrodes 31A, 31B formed of a metal selected form the group consisting of electrically conductive Ag, Cu, Pt and the like and alloys thereof or pastes containing said metal or semiconductors, such as $IrO_2$ and $SnO_2$, formed on a lower surface thereof by physical plating methods, such as the vacuum coating method and the CVD method, or the chemical plating methods, such as the electrolytic method and the electroless plating method, or the printing methods, such as the silk screen printing method, the relief printing method and the flat plate printing method.

And, base end portions positioned at one end edge portion of the substrate 30 of the respective electrodes 31A, 31B serve as lead portions 32A, 32B as they are, another almost circular pointed end portions positioned in an almost central portion of the substrate 30 being formed in the form of internal electrodes 33A, 33B coated with electrode materials, such as AgCl, (by the physical plating methods or the chemical palting methods or the printing methods), and one 33A of the internal electrodes (on the side of the pH-measuring electrode) being provided with a through hole 34, of which an inner surface has been subjected to a treatment for making it electrically conductive, as an electrode through hole formed at an almost center thereof. Reference numeral 35 designates a first support layer fixedly mounted on the upper surface of the substrate 30 and reference numeral 36 designates a second support layer fixedly mounted on the lower surface of the substrate 30. All of the se support layers 35, 36 are formed of materials having a sufficiently high electrical insulating property (for example polyethylene terephthalate) in the same manner as the substrate 30. Reference numeral 37 designates a gelatinized internal solution charged in the through hole of the first support layer 35 and is sealed up tightly by means of a flat plate ion-responsive membrane 38 fixedly mounted on the first support layer 35. The gelatinized internal solution 37 is obtained by adding gelatinizing agents (for example agar-agar, gelatin, glue, alginic acid, various kinds of hygroscopic polymer and the like) and evaporation-preventing agents (for example glycerin, ethylene glycol and the like) to a basic internal solution, which is obtained by adding a phosphoric acid buffer solution to a AgCl-supersaturated 3.3 N-KCl solution, and formed in the form of a thin plate. Reference numeral 39 designates a gelatinized internal solution on the side of the reference electrode having the same chemical composition as the above described gelatinized internal solution 37 and brought into contact with the internal electrode 33B through a through hole formed in the second support layer 36. A gel-impregnated hydrophobic high molecular porous member 540 passing through the first support layer 35, the substrate 30 and the second support layer 36 is provided in the vicinity of the internal electrode 33b so as to serve as a liquid junction. Reference numeral 41 designates a case for housing the above described first support layer 35, substrate 30, second support layer 36, gelatinized internal solution 39 and the like therein. Other constructions are the same as in the preferred embodiment shown in FIG. 5.

An operation of the above described pH-measuring apparatus for use in processes is substantially the same one as that shown in FIG. 2 excepting that 2 sets of a group of sheet-like composite electrodes A, A' are automatically changed over to a measuring condition (a condition in which the sample is flown through the groove 17) and an awaiting condition (a condition in which the sample is stopped to flow through the groove 17).

That is to say, under the condition that the sample is flown through the groove 17 on the right side, the measurement is conducted by means of 3 sheet-like composite electrodes A disposed in said groove 17, a mean value of measured values by these sheet-like composite electrodes A being computed, potential differences $\Delta$ pHx of the respective sheet-like composite electrodes A relative to said mean value being computed, and if said potential differences $\Delta$ pHx are within an allowable range (for example $\pm 0.1$ pH corresponding to about $\pm 6$ mV), said sheet-like composite electrodes are judged to be normal while if they exceed the allowable range, they are judged to be abnormal.

In the case where all of the sheet-like composite electrodes A have been judged to be normal, a mean value (pHm) of these measured values is converted into a pH unit to be put in the indicating portion 6. The process control is conducted on the basis of a signal put out from the indicating portion 6.

If any one of the sheet-like composite electrodes A is judged to be abnormal, the alarm 7 emits the maintenance alarm and simultaneously the sheet-like composite electrode, which has been judged to be abnormal, is excluded (the measured signal is cut), the measurement being continued by means of 2 remaining sheet-like composite electrodes A, the mean value being computed, and the process control being continued on the basis of the computed mean value.

And, when the maintenance alarm is emitted, the worker required for maintenance goes to the measuring spot to conduct the maintenance and the like of the sheet-like composite electrode, which has been judged to be abnormal, while the measurement is continued by means of 2 remaining sheet-like composite electrodes A.

In addition, although the measurement is conducted by 3 sheet-like composite electrodes, so that the maintenance alarm is emitted when the abnormality occurs in one sheet-like composite electrode, in the preferred embodiment shown in the drawing, in the case where the measurement is conducted by means of 4 or more sheet-like composite electrodes in the same manner as in the preferred embodiment shown in FIG. 1, the primary maintenance alarm is emitted at a point of time when the abnormality occurs in any one of the sheet-like composite electrodes, the sheet-like composite electrodes, in which the abnormality has occurred, being excluded in turn, and at a point of time when 2 electrodes remain active the secondary maintenance alarm, in short the original maintenance alarm, is then activated.

Furthermore, the group of the sheet-like composite electrodes existing under the awaiting condition is periodically calibrated. The characteristics (unsymmetrical electric potential, sensitivity, response speed) of the respective electrodes measured in said calibration are compared with the data (unsymmetrical electric potential, sensitivity, response speed) for judging a useful life time of the respective sheet-like composite electrodes obtained by the first calibration conducted when the apparatus was installed to judge whether the electrode should be exchanged or not.

That is to say, when a number of times when the respective groups of the sheet-like composite electrodes are changed over to the awaiting condition reaches an appointed number, said pump 27 is moved and the three-way valve $V_3$ is changed over, whereby the first standard solution and the second standard solution are flown through the groove 17 on the side of the electrode existing under the awaiting condition in this order, so that every sheet-like composite electrode can be calibrated to a zero point and sensitivity. In this calibration, the electrode characteristics, in short unsymmetrical electric potential, sensitivity and response speed, of every sheet-like composite electrode are measured and compared with the initial values (data for judging a useful life time). And, if the result of comparison (the degree of the change from the initial value) reaches the previously set control value, the exchange display lamp $7a'$ corresponding to said sheet-like composite electrode is lighted.

According to the present preferred embodiment, 2 sets of the group of electrodes are used in the same manner as in the preferred embodiment shown in FIG. 8, so that the sum total of times during the respective electrodes are actually used occupying in the operating time of the apparatus is reduced to half, whereby the maintenance period can be increased. In addition, an advantage occurs in that the use of the sheet-like composite electrodes can make the measuring apparatus light and compact on the whole.

Besides, although the pH-measuring apparatus was illustrated in the above described respective preferred embodiments, the present invention can be similarly applied also to the ion-measuring apparatus for measuring a concentration of other ions such as $Na+$ and $K+$.

Effects of the Invention

The present invention has the above described construction, so that the following effects can be given by the present invention.

(1) Since when the abnormality occurs in any one of the electrodes, the maintenance alarm is emitted but the electrode, which has been judged to be abnormal, is excluded to continue the measurement by means of the remaining normal electrodes and the spare electrodes, even though the maintenance alarm was emitted, in short the abnormality actually occurred in the electrode, the process control is not hindered, and as a result, the maintenance of the electrode can be conducted with a time to spare.

(2) Since the maintenance alarm is emitted at a point of time when the abnormality actually occurred in the electrode, it is not necessary to determine the maintenance period in such the manner that the maintenance is conducted before the abnormality occurs in the electrode, whereby the maintenance period can be increased.

(3) According to the invention spare electrode is held a the condition that it is not brought into contact with the sample during the normal measurement and is brought into contact with the sample when it is actually required, so that the deterioration of the spare electrode by hindrances, soils and the like contained in the sample can be prevented, whereby the maintenance period can be effectively increased.

(4) Two sets of the group of electrodes are used, so that the sum total of times during which the respective electrodes are actually used in the operating time of the apparatus is reduced to half, whereby by the maintenance period can be increased. The use of sheet-like composite electrodes can make the measuring apparatus light and compact. Not only the expense of the electrode can be reduced but also the standard electric potential is fixed by the common use of the reference electrode, whereby improving the accuracy of measurement.

What is claimed is:

1. An ion measuring apparatus for the monitoring of a sample from a production process, comprising:
   a plurality of ion measuring electrodes for respectively measuring the ion content of the sample and providing an output measurement signal based on outputs from each of the electrodes;
   means for determining a failure of one of the electrodes, and
   means for excluding the failed electrode output form the output measurement signal 2. The ion measuring apparatus of claim 11 further including a supplemental ion measuring electrode whose output signal is utilized to replace the output of the failed electrode.

3. The ion measuring apparatus of claim 2 further including means for automatically activating the supplemental ion measuring electrode upon a failure of an electrode.

4. The ion measuring apparatus of claim 2 wherein an initial set of ion measuring electrodes are provided and means are provided to replace the set of ion measuring electrodes with a supplemental set of ion measuring electrodes upon detection of a failure of any one of the set of ion measuring electrodes.

5. The ion measuring apparatus of claim 2 further including means for moving the supplemental ion measuring electrode into the sample after detection of a failure.

6. The ion measuring apparatus of claim 1 wherein the ion measuring electrodes are in the form of sheet electrodes.

7. The ion measuring apparatus of claim 1 wherein the ion measuring electrodes are in the form of rod-like composite electrodes integrally comprising an ion-selective electrode and a reference electrode.

8. The ion measuring apparatus of claim 7 including a second alarm for providing an indication of a second failure of an electrode and means for enabling a second alarm mode of operation after the initial detection of a failure.

9. The ion measuring apparatus of claim 1 further including an alarm that is responsive to a detection of a failure of an electrode.

10. An ion measuring apparatus for continuously monitoring samples form a production process, comprising:
    a plurality of duplicate ion measuring electrodes for measuring a predetermined ion concentration characteristic of the sample;
    means for calibrating each of the ion measuring electrodes;
    first means of determining any failure of the electrodes;
    second means, in response to the determination of a failure by the first means, for determining whether a sufficient number of electrodes are still accurately measuring the sample, and
    means for excluding the failed ion measuring electrode and continuing the measurement of the sample when the second determining means indicates that an accurate measurement can be continued with the remaining electrodes.

11. The ion measuring apparatus of claim 10 wherein the plurality of duplicate ion measuring electrodes includes at least one replacement electrode and means for activating the replacement electrode to take the place of the failed electrode.

12. The ion measuring apparatus of claim 10 further including means responsive to the failure determining first means for providing an alarm signal.

13. The ion measuring apparatus of claim 10 further including a supplemental ion measuring electrode whose output signal is utilized to replace the output of the failed electrode.

14. The ion measuring apparatus of claim 10 wherein the ion measuring electrodes are in the form of sheet electrodes.

15. The ion measuring apparatus of claim 10 wherein the ion measuring electrodes are in the form of rod-like composite electrodes integrally comprising an ion-selective electrode and a reference electrode.

16. An ion measuring apparatus for the monitoring of a sample from a production process, comprising:
    a plurality of ion measuring electrodes for respectively measuring the ion content of the sample and providing an output signal from each of the electrodes;
    means for computing a mean value signal from the output signals of each of the electrodes as a measurement signal;
    means for judging a failure of any one of the electrodes to profile a reliable output signal;
    means for excluding the failed ion measuring electrode output signal from the mean value computation;
    warning means for providing an indication of a failure, and
    means for using he output signals from the remaining ion measuring electrodes after the failure judgment to maintain a continuous measurement signal, whereby the production process can continue despite the failed electrode.

17. The ion measuring apparatus of claim 16 wherein the warning means includes a secondary alarm that is enabled after an initial alarm.

18. The ion measuring apparatus of claim 16 further including means for determining whether a sufficient number of electrodes ar still accurately measuring the sample.

19. The ion measuring apparatus of claim 16 further including a supplemental ion measuring electrode whose output signal is utilized to replace the output of the failed electrode.

20. The ion measuring apparatus of claim 19 further including means or automatically activating the supplemental ion measuring electrode upon a failure of an electrode.

21. The ion measuring apparatus of claim 20 further including means for moving the supplemental ion measuring electrode into the sample after detection of a failure.

22. The ion measuring apparatus of claim 16 wherein the ion measuring electrodes are in the form of sheet electrodes.

23. The ion measuring apparatus of claim 16 wherein the ion measuring electrodes are in the form of rod-like composite electrodes integrally comprising an ion-selective electrode and a reference electrode.

24. The ion measuring apparatus of claim 16 wherein an initial set of ion measuring electrodes are provided and means are provided to replace the set of ion measuring electrodes with a supplemental set of ion measuring electrodes upon detection of a failure of any one of the set of ion measuring electrodes.

* * * * *